US010076292B2

(12) United States Patent
Tkaczyk et al.

(10) Patent No.: US 10,076,292 B2
(45) Date of Patent: Sep. 18, 2018

(54) SYSTEMS AND METHODS FOR X-RAY TOMOGRAPHY HAVING RETROGRADE FOCAL POSITIONING

(71) Applicant: General Electric Company, Schenectady, NY (US)

(72) Inventors: John Eric Tkaczyk, Niskayuna, NY (US); Remy Andre Klausz, Yvelines (FR); Biju Jacob, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 272 days.

(21) Appl. No.: 14/885,383

(22) Filed: Oct. 16, 2015

(65) Prior Publication Data
US 2017/0105687 A1    Apr. 20, 2017

(51) Int. Cl.
*A61B 6/00* (2006.01)
*A61B 6/02* (2006.01)
(Continued)

(52) U.S. Cl.
CPC ............ *A61B 6/4021* (2013.01); *A61B 6/025* (2013.01); *A61B 6/4028* (2013.01); *A61B 6/502* (2013.01); *A61B 6/5205* (2013.01); *A61B 6/54* (2013.01); *G06T 11/005* (2013.01); *A61B 6/466* (2013.01); *H01J 35/24* (2013.01)

(58) Field of Classification Search
CPC ................................................... A61B 6/4021
See application file for complete search history.

(56) References Cited

U.S. PATENT DOCUMENTS 5,173,852 A    12/1992 Lonn
6,256,369 B1    7/2001 Lai
(Continued)

FOREIGN PATENT DOCUMENTS

CN    102867294 A    1/2013
EP    2407109 A1    1/2012
(Continued)

OTHER PUBLICATIONS

Zhou, Zhongxing et al., "Application of Fourier-wavelet regularized deconvolution for improving image quality of free space propagation x-ray phase contrast imaging.", Phys Med Biol., vol. 57, Issue 22, (2012), (pp. 7459-7579, 21 pages total).
(Continued)

*Primary Examiner* — Dani Fox
(74) *Attorney, Agent, or Firm* — GE Global Patent Operation; Pabitra Chakrabarti

(57) ABSTRACT

A tomography apparatus includes a multi-focal point x-ray source, a support to travel a trajectory path, a detector having a plurality of pixels, where one of the multi-focal point x-ray source, the detector, and an item-under-test move on the support. A control processor controls a change in the focal point of the x-ray source at discrete points, or continuously, within a measurement region, the focal point change in a direction retrograde to the support arm travel, a detector memory accumulates a digital value representative of a signal charge from at least a portion of the plurality of pixels, the control processor reconstructs a volumetric image of the item-under-test by processing the detector memory contents. A method for continuous tomosynthesis and a computer-readable medium are also disclosed.

20 Claims, 7 Drawing Sheets

(51) Int. Cl.
*G06T 11/00* (2006.01)
*H01J 35/24* (2006.01)

(56) References Cited

U.S. PATENT DOCUMENTS

| | | |
|---|---|---|
| 6,754,298 B2 | 6/2004 | Fessler |
| 6,940,943 B2 | 9/2005 | Claus et al. |
| 7,212,606 B2 | 5/2007 | Souchay et al. |
| 7,244,063 B2 | 7/2007 | Eberhard et al. |
| 8,229,199 B2 | 7/2012 | Chen et al. |
| 8,246,543 B2 | 8/2012 | Johnson et al. |
| 8,340,388 B2 | 12/2012 | Rosentengel |
| 2006/0008047 A1 | 1/2006 | Zhou et al. |
| 2009/0161815 A1 | 6/2009 | Grass et al. |
| 2010/0128958 A1 | 5/2010 | Chen et al. |
| 2010/0284596 A1 | 11/2010 | Miao et al. |
| 2010/0322498 A1 | 12/2010 | Wieczorek et al. |
| 2011/0188624 A1 | 8/2011 | Ren et al. |
| 2012/0020450 A1 | 1/2012 | Jung et al. |
| 2012/0300901 A1 | 11/2012 | Lewalter et al. |
| 2014/0205073 A1 | 7/2014 | Tkaczyk et al. |
| 2015/0332485 A1 | 11/2015 | Klausz et al. |

FOREIGN PATENT DOCUMENTS

| | | |
|---|---|---|
| WO | 2009122328 A1 | 10/2009 |
| WO | 2014011681 A2 | 1/2014 |

OTHER PUBLICATIONS

Lyuboshenko, Igor et al., "Stable Signal and Image Reconstruction from Noisy Fourier Transform Phase", IEEE Transactions on Signal Processing, vol. 47, No. 1, Jan. 1999, (pp. 244-250, 7 total pages).

Qian, Xin et al., "High resolution stationary digital breast tomosynthesis using distributed carbon nanotube x-ray source array", Medical Physics, Apr. 2012, 39(4), DOI: 10.1118/1.3694667, PMCID: PMC3321055, (pp. 2090-2099, 10 total pages).

Qian et al., "Design and Characterization of a Spatially Distributed multibeam Field Emission X-Ray Source for Stationary Digital Breast tomosynthesis", Medical Physics, Volume No. 36, Issue No. 10, pp. 4389-4399, Sep. 34, 2009.

Travish et al., "Applying high frame-rate digital radiography and dual-energy distributed-sources for advanced Tomosynthesis", Medical Applications of Radiation Detectors III, Proc. of SPIE, Volume No. 8853, Aug. 25, 2013.

International Search Report and Written Opinion issued in connection with corresponding PCT Application No. PCT/US2016/057070 dated Jan. 2, 2017.

SYSTEMS AND METHODS FOR X-RAY TOMOGRAPHY HAVING RETROGRADE FOCAL POSITIONING

BACKGROUND

Digital breast tomosynthesis (DBT) is an imaging technique that allows a volumetric reconstruction of the whole breast from a finite number of projections obtained by different x-ray source angles. DBT is an important tool used for screening and diagnostic mammography. This technique involves taking a series of x-ray images (projections, also called views) with the x-ray source at different positions while the detector and breast are relatively stationary. The source emits x-rays from a focal spot location in the source. At any point in a DBT scan, a line between the focal spot and the center of the detector defines a projection angle relative to a direction perpendicular to the detector plane. The projection angle should be relatively constant during acquisition of the image in order to map features in the breast to a relatively fixed locations on the detector. In conventional DBT the x-ray source makes an arc, during which a series of images is acquired at different relatively fixed projection angles. Alternately, the x-ray source can move along a linear path as is practiced today for a chest tomography, a related 3D imaging method. In another approach, the x-ray source remains stationary and the detector is moved along a predetermined path. During the motion of the x-ray source, a static or dynamic collimator stationed at the x-ray source exit will direct the x-ray field so as to illuminate only the area of the detector. The acquired data is processed by a computer, where a reconstruction algorithm combines the projections from known projection angles to obtain sectional views of the breast.

Current systems use either a step-and-shoot configuration, where the x-ray source (or detector) is stationary during x-ray exposure, or a continuous motion configuration, where the x-ray source (or detector) is constantly moving but the x-rays are pulsed during the motion. In the former configuration the relatively fixed projection angle is ensured by the stationary source location; in the latter configuration the projection angle is ensured by the short temporal duration of the pulse. The number of x-ray exposure cycles corresponds to the number of stationary positions or to the number of pulses respectively. In one-to-one correspondence with X-ray exposure cycles are the detector frames, each of which includes an integration and read period. The detector integration period temporally overlaps the corresponding x-ray exposure cycles. Subsequent to the x-ray exposure cycle, the detector read periods is when x-ray data is transferred into digital memory. During the time between each cycle, the x-ray intensity is zero so as to allow the system to move to the next angle location. The detector read periods typically occur during this time between cycles. Movement between locations is often at a higher velocity than the velocity while the x-ray is being pulsed. In both these cases the x-ray source is not run at full duty cycle, being off at least long enough to read out the detector and to move system components into the next angle position.

In continuous motion systems with a pulsed x-ray source there is substantial image blurring that occurs because a single detector integration period is acquired while the x-ray source (or detector) is moving during the x-ray exposure. To minimize this blurring, one option is to increase the x-ray source power and pulse with shorter exposure times. Higher power x-ray sources can cost more and weigh more and release more heat into the system. The higher weight leads to additional system cost since larger motors and more rigid gantries are needed.

DETAILED DESCRIPTION

In accordance with some embodiments, systems and methods provide a tomosynthesis system that includes a multi-focal point x-ray source (which at a minimum includes an electron beam and an anode target) that can be moved relative to both the object to be imaged and the detector. In one implementation, the object and detector do not move relative to each other, though in other implementations they could. The x-ray source follows a path. For example, a line or arc, though other more complicated paths can be envisioned. The moving x-ray source generates a sequence of x-ray emission cycles that are coordinated with the detector readout so as to acquire a rapid succession of x-ray image projections while switching, and/or scanning the focal point of the source in a direction retrograde (i.e., counter) to the source's mechanical motion.

The instantaneous x-ray field intensity may or may not change over the range of motion. The programmed intensity profile generates x-rays either continuously at constant amplitude with variable intensity, or pulsed along this path in order to effect the number of x-ray cycles possibly with zero intensity periods between cycles. As the instantaneous x-ray field transverses the object the field is attenuated. The transmitted, attenuated x-ray field is then detected by an x-ray detector.

Figure 1:
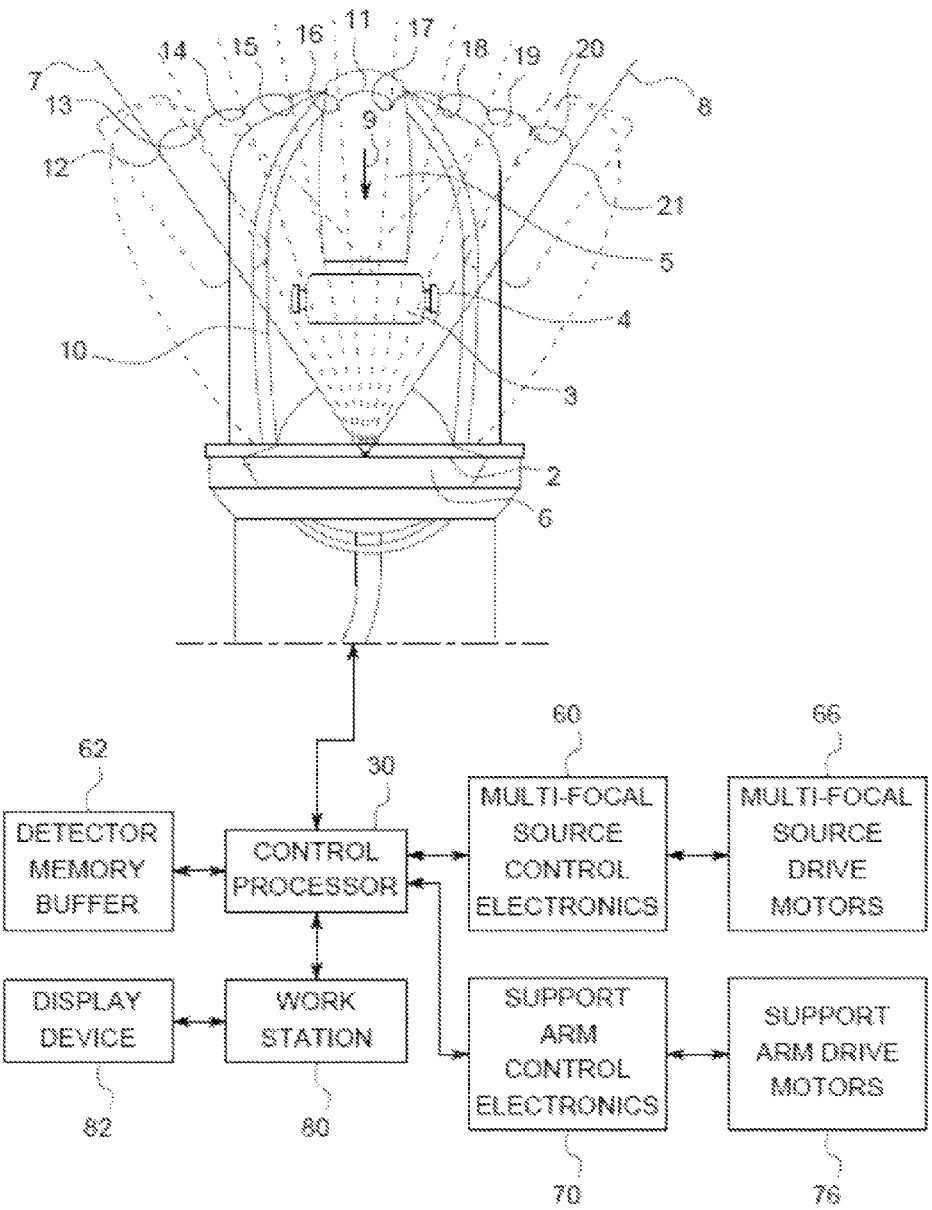
FIG. 1 depicts a radiographic projection tomography apparatus in accordance with embodiments.

FIG. 1 depicts radiographic projection tomography apparatus 1 in accordance with some embodiments. Tomography apparatus 1 includes support 2 that can support an item-under-test, i.e., the object to be subjected to tomography. In one implementation, the tomography apparatus can be configured as a mammography apparatus wherein support 2 is a breast-holder support that supports a patient's breast. Nevertheless, any other implementation for a tomography apparatus can be envisaged. The item-under-test is placed on the support and, for example if a patient's breast, compressed by paddle 3 which can be maneuvered by an operator using for example handles 4.

Tomography device 1 furthermore comprises a source of radiation, such as multi-focal point x-ray source 5—i.e., a source that can have its focal point adjusted under control signal direction, and detector 6. The multi-focal point x-ray source can be implemented as a separate anode/cathode set per position (e.g., multi-spot with a thermionic, dispenser or field emitter); a multi-cathode with a shared moving-anode; or as a scanning source by scanning a cathode-produced electron beam across the surface of the anode. The detector is capable of detecting the x-rays after they have crossed the item-under-test. The detector 6 is placed beneath support 2. In practice, paddle 3 is made of an x-ray transparent material (e.g., plastic).

In accordance with one implementation, paddle 3, the item-under-test, support 2, and detector 6 are in fixed position, while the x-ray source 5 may take up several positions in space relative to this assembly. In other implementations, the detector can travel in relation to the x-ray source. In still other implementations, both the x-ray source and the detector can move in a coordinated pattern relative to the patient's breast.

Tomography device 1 includes control processor 30 which executes computer readable instructions to control the operation of device 1. Control processor 30 obtains detector data from addressable detector memory buffer 62. This data can be used by the control processor to reconstruct an image. In other embodiments, the detector data can be provided to work station 80, which can reconstruct the image. Display device 82 displays the reconstructed image.

A support of the source 5, such as an arm, can be provided and configured to move the source along some trajectory between extreme positions 7 and 8. In some embodiments, such as for linear motion, the source motion is controlled to follow a track. Control processor 30 provides control signals to support arm control electronics unit 70. These control signals are provided to drive motors 76, which move the support arm. The drive motors can include positional encoders, synchros, etc., which provide positional feedback that is forwarded to control processor 30. The control processor also provides control signals to multi-focal source control electronics unit 60. These control signals are provided to drive motors 66, which move the focal point of the x-ray source and the angle of the x-ray source in relation to the support arm and the item-under-test. Both sets of drive motors 66, 76 can include positional encoders (linear or rotary), synchros, etc., which provide positional feedback that is forwarded to control processor 30.

As disclosed above, the support arm can move the x-ray source relative to the detector and item-under-test; the detector relative to the x-ray source and item-under-test; and/or both the x-ray source and the detector can move relative to the item-under-test (an implementation that can require an additional support arm, associated controls, and drive motors).

In particular, FIG. 1 shows distributed in reorientation between a first extreme position 7 and a second extreme position 8 that are, for example, symmetrical relative to each other relative to a bisecting direction 9. The positions are on the whole distributed on an arc of a circle. In the depicted implementation, support arm 10 carries x-ray source 5. There are other possible arrangements enabling the x-ray source and/or the detector to shift in a plane, along a line, or a sphere portion.

X-ray source 5 is provided with first focal point 11 that is the x-ray emitting focal point. For a multiplicity of exposure positions, herein represented by ten positions numbered 12 to 21, the number of these positions being greater than or equal to 3, is related to tomography apparatus device whose x-ray source is at a halt at the first extreme position 7 and, after regular exploration, is at a halt at the second extreme position 8.

On the path, the positions can be distributed evenly. With image reconstruction processing corrections, positions 12 to 21 need not be evenly distributed. In accordance with one embodiment, image data can be sampled at regular intervals along the arc of motion, i.e., in and around the positions 12 to 21.

In accordance with embodiments, the object of interest is exposed to one or multiple x-rays shots that extend over multiple image readouts. Signal charge is accumulated in the detector pixels and periodic readout events read the charge from the pixels into a digital image frame stored in detector memory buffer 62.

The detector can be operated in either a continuous readout (rolling shutter) mode, or in a charge storage mode (i.e., frame buffer mode, or global shutter). In the continuous readout mode all the pixels within a subset of all the pixels are read in parallel and different subsets of pixels are read sequentially. In the charge storage mode all the charge stored on the pixels are simultaneously transferred to storage capacitors before readout. Then readout of the storage capacitors occurs while the next frame is acquired by accumulation of signal charge onto the pixels.

Embodying systems are simpler, lower-cost DBT systems than conventional step-and-shoot DBT systems because of the simplified mechanical requirements needed to implement these embodiments. The improved duty cycle operation of the x-ray source achieves a lower x-ray source current to develop a total radiation dose required to obtain a quality image. Accordingly compared to a continuous motion system with a pulsed x-ray source exposing individual images, embodying systems have a reduced thermal requirement for the x-ray source resulting in lower cost. Embodying systems eliminate image blurring during the x-ray exposure by providing a sufficient multitude of detector reads so that object positions are projected to detector locations between adjacent views that are within one detector pixel pitch.

In either detector readout mode (continuous readout mode or charge storage mode), each pixel will integrate signals from the x-ray field only for as long as it takes to readout the detector. Detectors that show fast frame rate capability include CMOS and amorphous-indium-gallium-zinc-oxide active pixel arrays. Fast digital methods for analog-to-digital conversion of signal charge are recently available from low cost and low power integrated electronics. Application specific integrated circuits (ASICs) and on-detector electronics can effectively read at frame rates of 30 to 1000 frames-per-sec. The short time for the signal charge integration can minimize blurring of object positions on the detector, reduce the total exam time, and provide the maximal amount of projection data to use in a tomographic reconstruction.

In accordance with some embodiments, the high rate of projection data acquisition provides fine sampling of the relative angle position of the x-ray source (or detector). Furthermore, the simplified support arm mechanics and overall fast time needed to complete an angular scan allows a wider angular range. The angular difference between first extreme position 7 and second extreme position 8 (FIG. 1) can be wider without introducing blur due to x-ray source motion. The result of this maximal amount of projection data when used in tomographic reconstruction can create volumetric images with higher spatial resolution and better separation of tissues in regards to their distance from the detector. Fast scan time can minimize the potential for patient motion during the scan that otherwise would create non-consistent views of the object under test.

Figure 2:
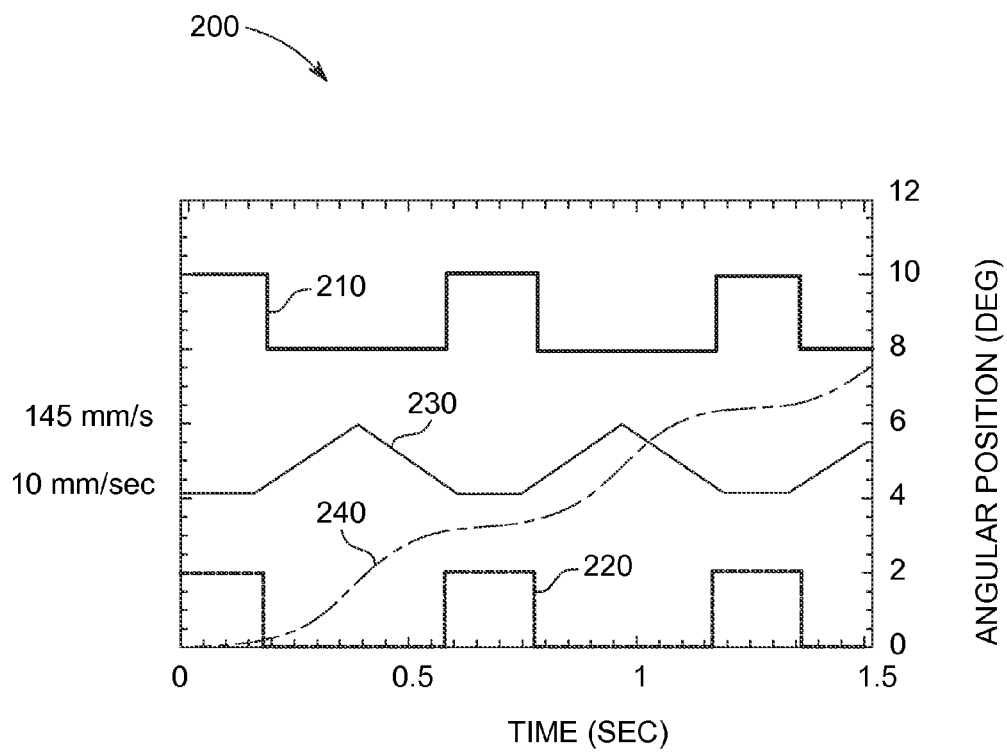
FIG. 2 depicts a conventional timing diagram for tomographic data acquisition.

FIG. 2 depicts conventional timing diagram 200 for tomographic data acquisition implementing a conventional continuous motion configuration. X-ray pulses 210 are periodically emitted by an x-ray source to expose the item-under-test. Coincident with the emission of x-ray pulses, during detector sampling window 220, one frame of detector data is obtained for each pulse 210. Support arm velocity 230 indicates that the support arm is moving between a first speed of 10 mm/sec, and a second speed of 145 mm/sec. The first speed is a minimal velocity maintained during the x-ray emission window so that measurements can be taken with minimal blurring. Between emission windows, the support arm is accelerated to move to the next position reaching its maximum velocity of the second speed prior to de-accelerating when approaching the next read position. Distance traveled curve 240 is representational of the distance the support arm moves over time from its start location (e.g., first extreme position 7 (FIG. 1)), to its end position (e.g., second extreme position 8 (FIG. 1)). As indicated by distance traveled curve 240 the support arm is in continuous motion with the least travel distance accumulated during each of the x-ray emission periods.

In accordance with embodiments, a high average velocity of multi-focal point x-ray source 5 along its tomographic trajectory path can be accommodated without image blurring occurring in the reconstructed image. This image clarity can be obtained by acquiring a rapid succession of x-ray image projections while switching and/or scanning the focal point of source 5 in a direction retrograde to the source's mechanical motion. Control processor 30 can coordinate the x-ray source mechanical motion and detector integration periods with the timing of x-ray emissions at different focal points of the multi-focal source. The control processor also coordinates the different focal points with the integration periods and mechanical motion of the x-ray source.

In an embodiment, one or more x-ray emission and detector integration periods can occur during slow-velocity segments of source trajectory. In order to lower the data bandwidth, detector memory buffer 62 can accumulate data flow. Readout of data in the detector buffer can occur during the entire scan period for the trajectory sweep. Each detector integration period can create a projection image that can be combined algorithmically to achieve the tomographic reconstruction view for the item-under-test.

Figure 3:
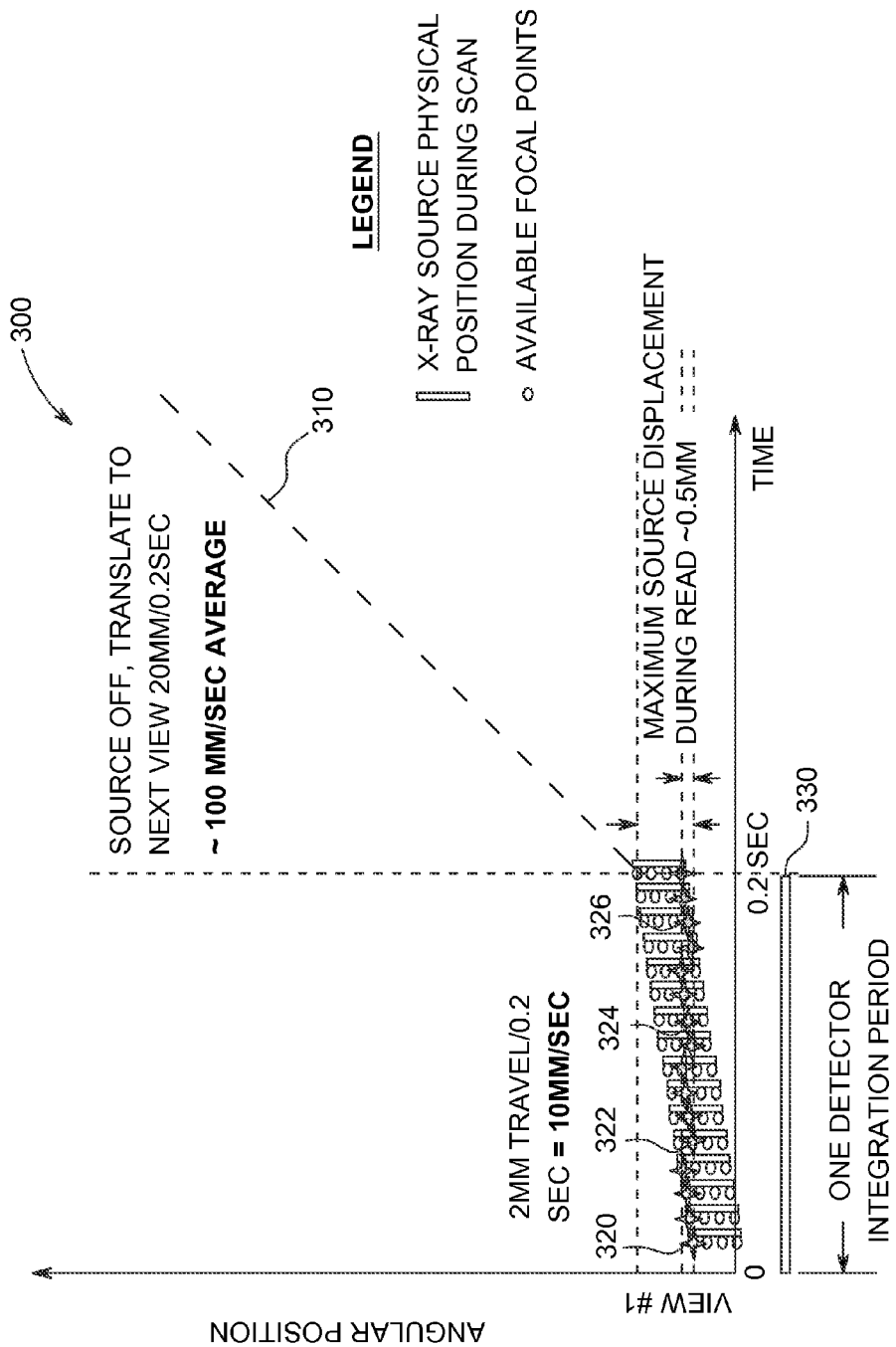
FIG. 3 depicts a timing diagram for a radiographic projection tomography apparatus in accordance with embodiments.

FIG. 3 depicts timing diagram 300 for a radiographic projection tomography apparatus having a multi-focal x-ray source having four focal points in accordance with embodiments. The four focal points within the source are positioned at relative angular positions 320, 322, 324 and 326. During scans between extreme positions trajectory path 310 is followed. The depicted trajectory path velocity is linear (about constant velocity) between the detector view positions. However, embodying systems are not so limited and non-linear velocity between the view periods is within the scope of this disclosure.

During view periods (while x-ray is emitting) measurements are taken at a slow speed of about 10 mm/sec for about 0.2 seconds (travel distance along trajectory path equals about 2 mm). Between emission periods, the speed is increased to about 100 mm/sec average while translating position to the next view location (travel distance along trajectory path equals about 20 mm during about 0.2 seconds).

In accordance with embodiments, during the detector integration period the focal point of the multi-focal x-ray source is switched under instruction from the control processor four times between focal points 320, 322, 324, 326. Alternately, the focal spot is scanned continuously in positions passing through the focal spot points. In accordance with embodiments, the scanning regime is selected so that the focal point of the source is retrograde to the direction of its travel along trajectory path 310. The embodying focal point switching results in a more uniform position of the x-ray source focal point along the detector during the integration period. A single frame measurement is obtained by detector 330 by integrating for 0.2 sec during the changing source location due to the combined mechanical source motion and switched position of the focal spot position.

Because of focal point switching of the multi-focal point source, the maximum focal displacement relative to the detector 330 during the integration period is about 0.5 mm, which is approximately slightly larger than the focal spot width. Estimates based on calculations indicates that this size focal displacement provides an acceptable degradation level of the detective quantum efficiency (DQE) and modulation transfer function (MTF) image quality metrics to result in no significant loss of low contrast detectability nor image blurring of the reconstructed image.

Figure 4:
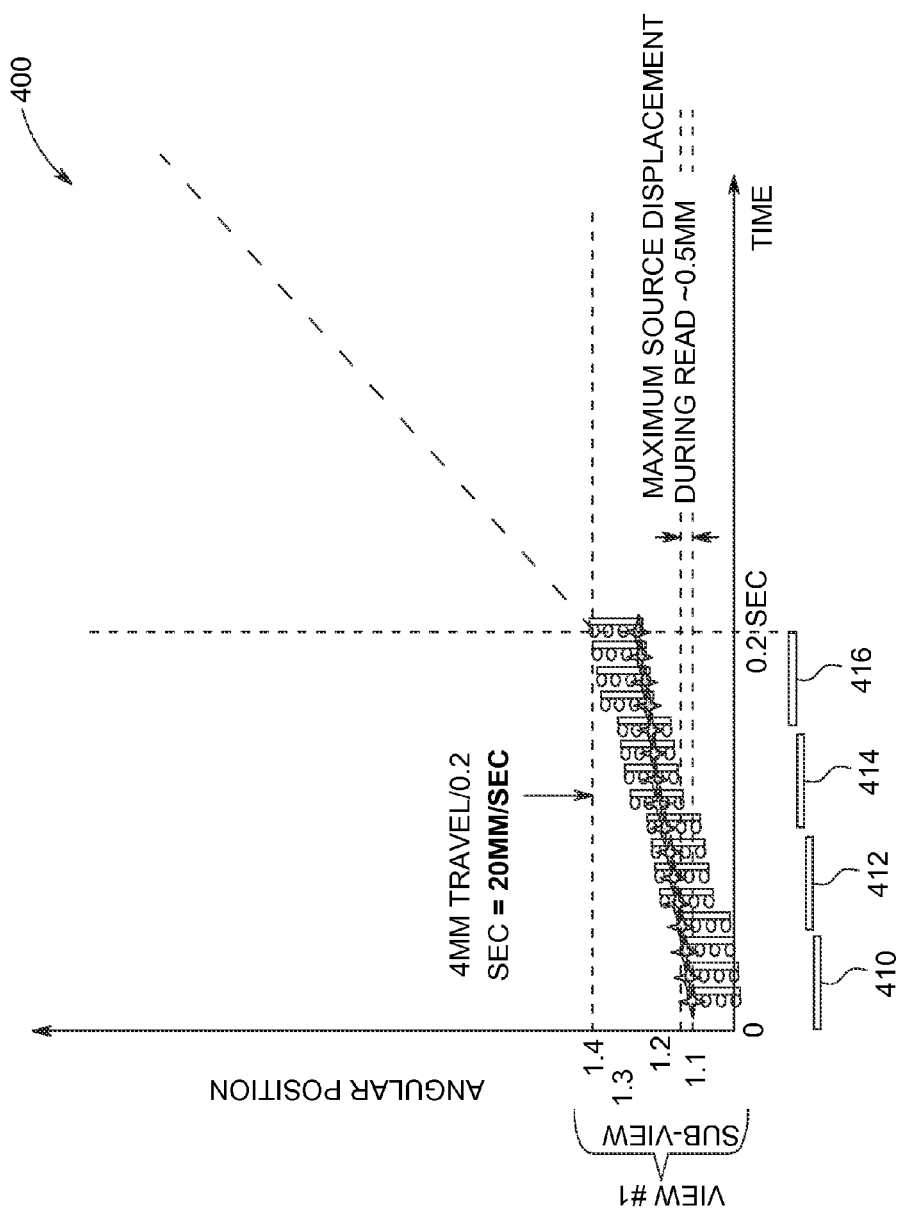
FIG. 4 depicts a timing diagram for a radiographic projection tomography apparatus in accordance with embodiments.

FIG. 4 depicts timing diagram 400 for a radiographic projection tomography apparatus having a multi-focal x-ray source having four focal points in accordance with embodiments, where four detector reads 410, 412, 414, 416 are obtained during the x-ray emission period. These four detector reads are obtained by reading from a single detector four times in about 0.05 second intervals (when the trajectory path velocity is about 20 mm/sec. An embodying system includes the four focal point multi-focal source in combination with a fast detector to result in shorter scan due to the higher trajectory path velocity during x-ray emission.

In accordance with this embodiment, during view periods measurements are taken at a faster speed of about 20 mm/sec for about 0.2 seconds (travel distance along trajectory path equals about 4 mm). Between emission periods, the speed is increased to about 100 mm/sec average while translating position to the next view location (travel distance along trajectory path equals about 20 mm during about 0.2 seconds). Embodying systems are able to maintain the maximum focal displacement relative to the detector of about 0.5 mm.

In accordance with embodiments, to achieve the four readouts the multi-focal point source is in combination with a fast detector so that four integration periods can be obtained during the x-ray emission period. In accordance with embodiments, the source focal point is switched at the boundary of each integration period.

In accordance with embodiments, during the detector integration periods the focal point of the multi-focal x-ray source is switched under instruction from the control processor four times. In accordance with embodiments, the scanning regime is selected so that the focal point of the source is retrograde to the direction of its travel along the trajectory path.

Detector reads 410, 412, 414, 416 have successively different focal points that are scanned retrograde to the trajectory path direction. The coordinated movement creates four closely spaced sub-view positions 1.1, 1.2, 1.3, 1.4 at each view. This can be contrasted with one view position achieved at a slower velocity as depicted in FIG. 3. During image reconstruction, these sub-views can be utilized to form the tomographic representation of the object under test.

Figure 5:
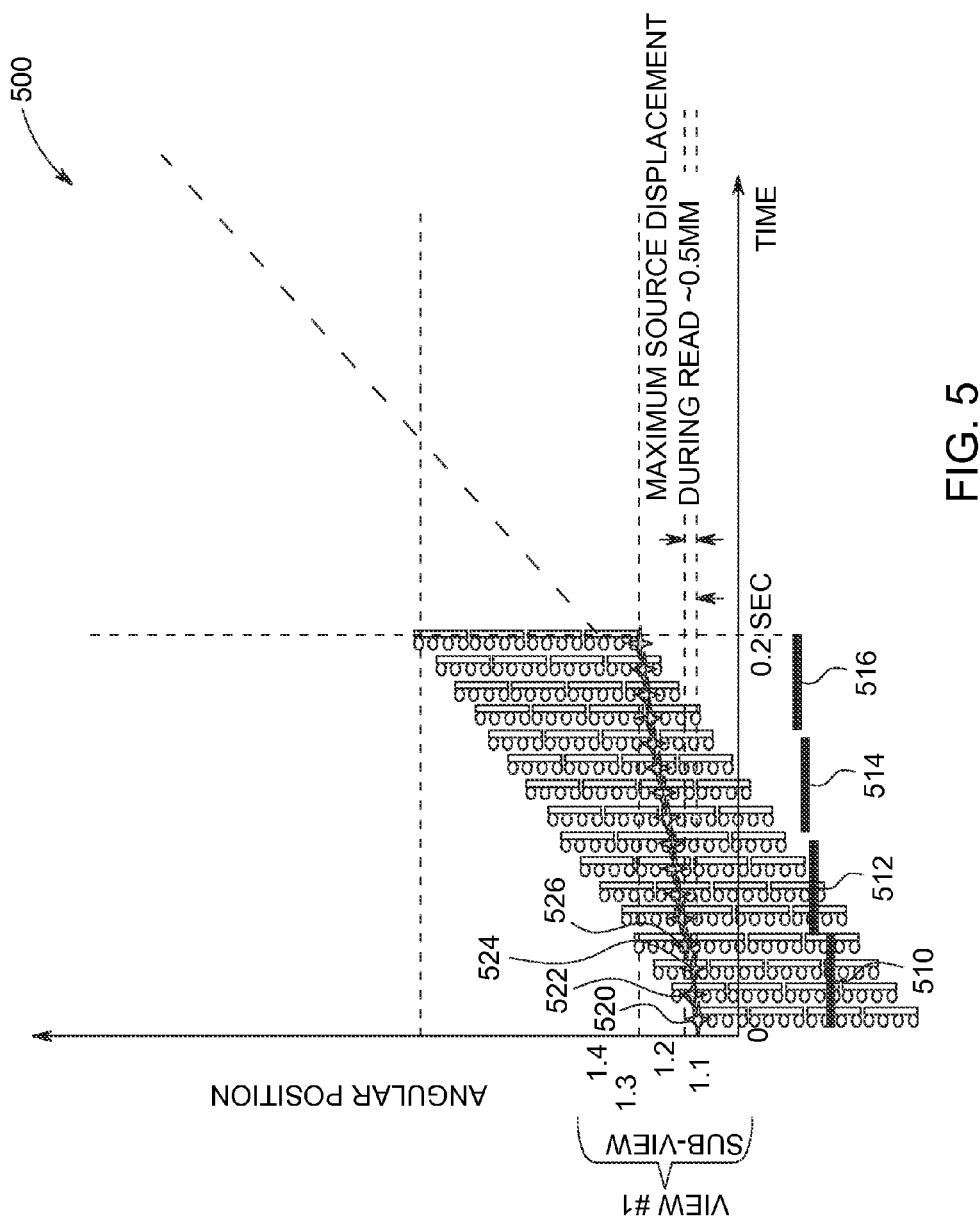
FIG. 5 depicts a timing diagram for a radiographic projection tomography apparatus in accordance with embodiments.

FIG. 5 depicts timing diagram 500 for a radiographic projection tomography apparatus having a multi-focal x-ray source having sixteen focal points in accordance with embodiments, where four detector reads 510, 512, 514, 516 are obtained during the x-ray emission period. The sixteen focal points are arrayed in four groups of four focal spot positions 520, 522, 524, 526. An embodying system includes multi-focal point x-ray source 5 having sixteen focal points in combination with a fast detector.

In accordance with embodiments, the trajectory speed during x-ray emission measurement period can be maintained at about 40 mm/sec (which equates to about 8 mm in about 0.2 seconds). This higher measurement speed can be achieved by switching among focal points 520, 522, 524, 526 at each of the four reads during detector reads 510, 512, 514, 516. A different array grouping of four focal spot positions are activated during the four reads.

In accordance with embodiments, during each of the detector read periods the focal point of the multi-focal x-ray source is switched under instruction from the control processor four times between focal points 520, 522, 524, 526. In accordance with embodiments, the scanning regime is selected so that the focal point of the source is retrograde to the direction of its travel along the trajectory path.

More granularity in the spacing between the focal points is obtained due to the sixteen focal positions of the embodying multi-focal x-ray source in coordination with the mechanical motion. Embodying systems are able to maintain the maximum focal displacement across the detector of about 0.5 mm during a read period. In between measurement positions the support arm can travel the trajectory path at about a maximum of 200 mm/sec.

Figure 6:
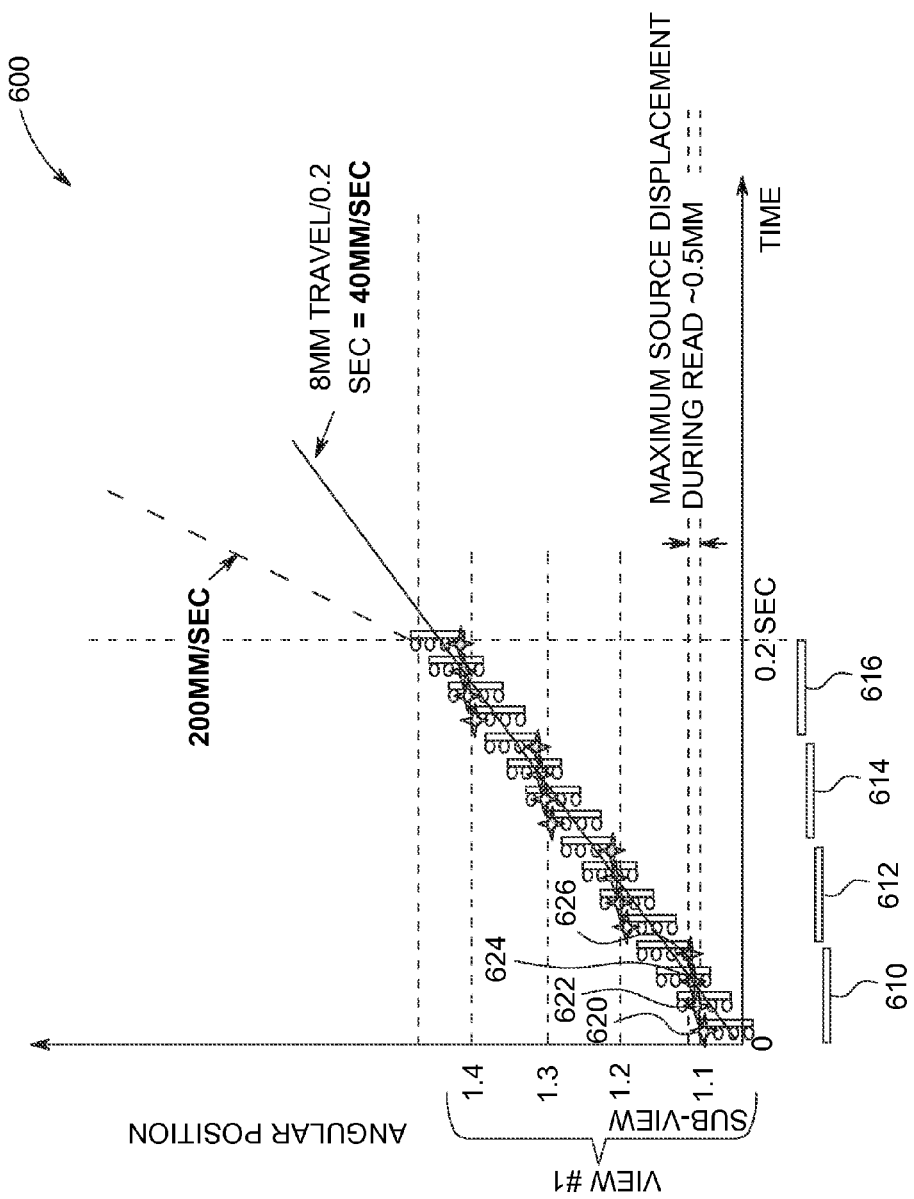
FIG. 6 depicts a timing diagram for a radiographic projection tomography apparatus in accordance with embodiments.

FIG. 6 depicts timing diagram 600 for a radiographic projection tomography apparatus having a multi-focal x-ray source having four focal points in accordance with embodiments, where four detector reads 610, 612, 614, 616 are obtained during the x-ray emission period. An embodying system includes multi-focal point x-ray source 5 having four focal points in combination with a fast detector.

In accordance with embodiments, during the detector read periods 610, 612, 614, 616 the focal point of the multi-focal x-ray source is switched under instruction from the control processor between focal points 620, 622, 624, 626. In accordance with embodiments, the scanning regime is selected so that the focal point of the source is retrograde to the direction of its travel along the trajectory path.

In accordance with embodiments, the trajectory speed during x-ray emission measurement period can be maintained at about 40 mm/sec (which equates to about 8 mm in about 0.2 seconds). Embodying systems are able to maintain the maximum focal displacement across the detector of about 0.5 mm. In between measurement positions the support arm can travel the trajectory path at about a maximum of 200 mm/sec.

An embodying system requires only four switching points, achieves a velocity of 40 mm/sec during the exposure period, and maintains a focal displacement that can obtain quality images with minimal blurring. In accordance with implementations, the focal point switching can be done electronically so that faster firing of the x-ray source can be achieved to maintain the high data acquisition rate. In accordance with this embodiment, sub-views 1.1, 1.2, 1.3, 1.4 are spread apart along the tomographic trajectory path. This physical separation of data can benefit the tomographic projection image by providing a more complete set of view angles by which the three-dimensional object structure is revealed in the reconstruction.

Figure 7:
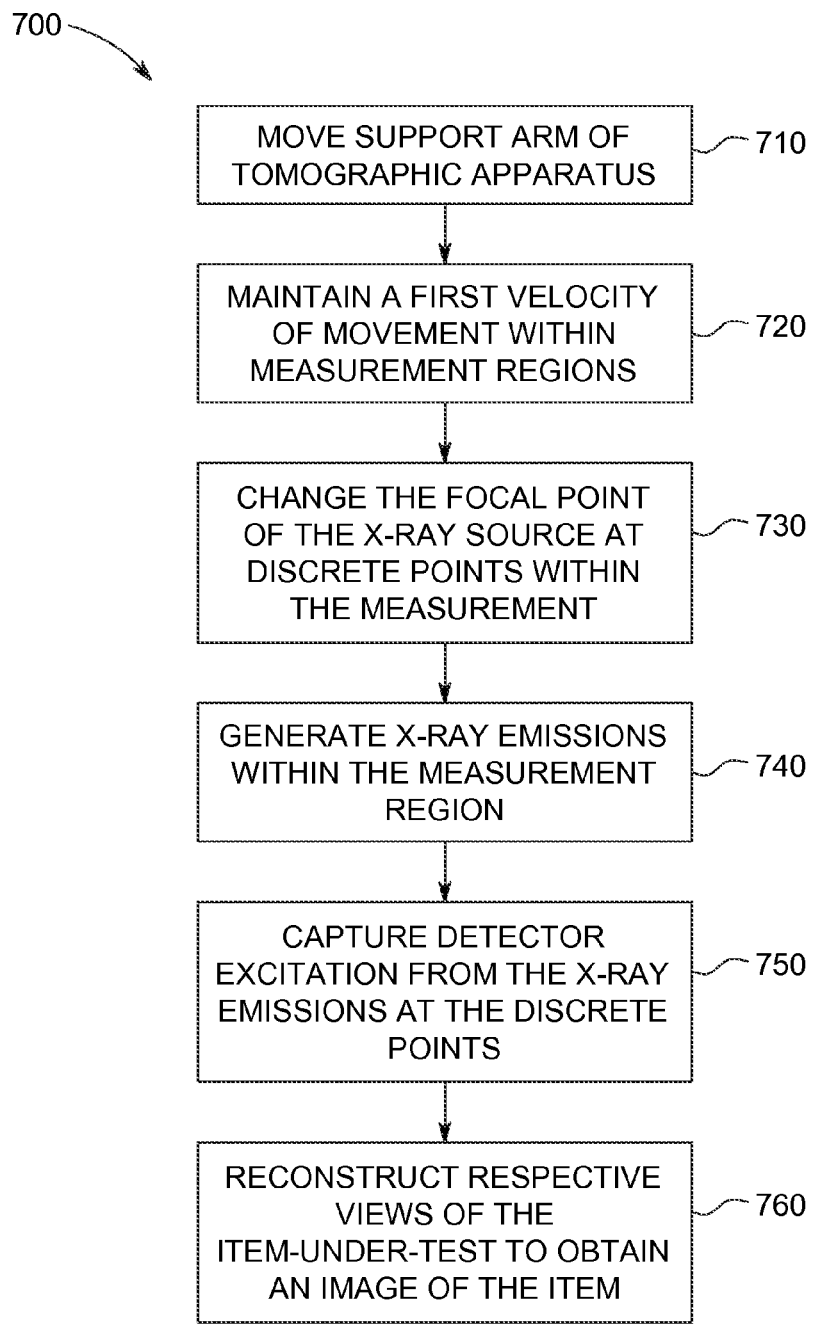
FIG. 7 depicts a process for obtaining radiographic projection tomography data in accordance with embodiments.

FIG. 7 depicts process 700 for obtaining radiographic projection tomography data using a multi-focal point x-ray source in accordance with embodiments. The support arm is moved, step 710, along its trajectory path from a first extreme position to a second extreme position. The support arm can move the x-ray source relative to the detector and item-under-test; the detector relative to the x-ray source and item-under-test; and/or both the x-ray source and the detector can move relative to the item-under-test.

Within a measurement region (i.e., a grouping of detector view periods) the velocity of the support arm is maintained, step 720, at about a constant rate. The time of a detector integration window within a measurement region can be the time of an expose period, or a portion of the expose period as disclosed above in FIGS. 3-6. Between measurement regions the support arm velocity can be increased to minimize test time. Within the measurement region the focal point of the multi-focal x-ray source changes, step 730, in a direction retrograde to the trajectory path. The changes in focal point can be at discrete points relative to the frame of reference set by the detector for various integration periods. The change in focal point maintains an overall displacement of the focal point in a measurement region to be within a predetermined amount—e.g., about 0.5 mm, although other displacements are within the scope of this disclosure.

X-ray pulses emissions are generated, step 740, with the measurement region(s). The excitation voltage output from the detectors is captured, step 750, at discrete points during the x-ray pulse. Respective views, and sub-views where captured, are reconstructed, step 760, to obtain an image of the item-under-test.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as obtaining radiographic projection tomography data by retrograde positioning of focal points of a multi-focal point x-ray source along the trajectory path, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A tomography apparatus comprising:
   a multi-focal point x-ray source;
   a support for the source configured to travel a predetermined trajectory path;
   a detector having a plurality of pixels, at least one of the multi-focal point x-ray source, the detector, and an item-under-test mounted on the support to move relative to one another;

a control processor configured to execute computer-readable instructions that cause the control processor to change the focal point of the x-ray source at discrete points within a measurement region in a direction retrograde to the support arm travel along the trajectory path, wherein the focal point of the x-ray source is changed at three or more discrete points and wherein displacement of the focal point is within a predetermined range along the measurement region of the trajectory path;

a detector memory configured to accumulate a digital value representative of a signal charge from at least a portion of the plurality of pixels exposed to a portion of the x-ray beam;

the control processor configured to reconstruct a volumetric image of the item-under-test by processing contents of the detector memory with a reconstruction process function.

2. The tomography apparatus of claim 1, including the control processor configured to provide control signals to a multi-focal source control electronics unit, the multi-focal source control electronics unit configured to control the multi-focal point x-ray source focal position.

3. The tomography apparatus of claim 1, the trajectory path extending from a first extreme position to a second extreme position, the control processor configured to provide velocity control signals to control the velocity of the support.

4. The tomography apparatus of claim 3, the velocity control signals set to a first velocity in measurement regions along the trajectory path, and a second velocity between measurement regions, the second velocity being greater than the first velocity.

5. The tomography apparatus of claim 4, the detector memory accumulating data during discrete measurement points within the measurement region.

6. The tomography apparatus of claim 1, the displacement of the focal point corresponds to focal spot width of the x-ray beam.

7. The tomography apparatus of claim 6, wherein maximum displacement of the focal point is within 0.5 mm.

8. A method of continuous motion tomosynthesis, the method comprising:

exposing an item-under test to a programmed intensity x-ray beam as one of a multi-focal x-ray source, a detector, and the item-under-test travel a pre-determined trajectory path, the detector having a plurality of pixels;

maintaining about a constant first velocity within a measurement region along the trajectory path;

changing a focal point of the multi-focal point x-ray source at discrete points along the measurement region in a direction retrograde to the travel along the trajectory path, wherein the focal point of the x-ray source is changed at three or more discrete points and wherein displacement of the focal point is within a predetermined range along the measurement region of the trajectory path;

accumulating in at least a portion of the plurality of pixels a signal charge from at least a portion of the x-ray beam;

recording in a detector memory buffer the accumulated signal charge from the plurality of pixels at discrete points, the signal charge recorded as digital frame images, the digital frame images representing raw baseline data; and reconstructing a volumetric image of the item-under-test by applying a reconstruction process function to the recorded digital frame images.

9. The method of claim 8, including providing control signals to a multi-focal source control electronics unit, the multi-focal source control electronics unit controlling the multi-focal point x-ray source focal position.

10. The method of claim 8, controlling velocity along the trajectory path from a first extreme position to a second extreme position to a first velocity in measurement regions and a second velocity between measurement regions, the second velocity being greater than the first velocity.

11. The method of claim 8, accumulating data at discrete measurement points within the measurement region.

12. The method of claim 8, the displacement of the focal point corresponds to focal spot width of the x-ray beam.

13. The method of claim 8, obtaining sub-views within the measurement region by reading the detector charges.

14. The method of claim 13, the focal point changing within a sub-view in an order repeated along the measurement region.

15. A non-transitory computer readable medium having stored thereon instructions which when executed by a processor cause the processor to perform a method of continuous motion tomosynthesis, the method comprising:

exposing an item-under test to a programmed intensity x-ray beam as one of a multi-focal x-ray source, a detector, and the item-under-test travel a pre-determined trajectory path, the detector having a plurality of pixels;

maintaining about a constant first velocity within a measurement region along the trajectory path;

changing a focal point of the multi-focal point x-ray source at discrete points along the measurement region in a direction retrograde to the travel along the trajectory path, wherein the focal point of the x-ray source is changed at three or more discrete points and wherein displacement of the focal point is within a predetermined range along the measurement region of the trajectory path;

accumulating in at least a portion of the plurality of pixels a signal charge from at least a portion of the x-ray beam;

recording in a detector memory buffer the accumulated signal charge from the plurality of pixels at discrete points, the signal charge recorded as digital frame images, the digital frame images representing raw baseline data; and reconstructing a volumetric image of the item-under-test by applying a reconstruction process function to the recorded digital frame images.

16. The non-transitory computer readable medium of claim 15, which cause the control processor to provide control signals to a multi-focal source control electronics unit, the multi-focal source control electronics unit controlling the multi-focal point x-ray source focal position.

17. The non-transitory computer readable medium of claim 15, which cause the control processor to control velocity along the trajectory path from a first extreme position to a second extreme position to a first velocity in measurement regions and a second velocity between measurement regions, the second velocity being greater than the first velocity.

18. The non-transitory computer readable medium of claim 15, which cause the control processor to accumulate data at discrete measurement points within the measurement region.

19. The non-transitory computer readable medium of claim 15, which cause the control processor to select the displacement of the focal point corresponding to the focal spot width of the x-ray beam.

20. The non-transitory computer readable medium of claim 15, which cause the control processor to obtain sub-views within the measurement region by reading the detector charges, and change the focal point within a sub-view in an order repeated along the measurement region.

* * * * *